United States Patent [19]

Rottig et al.

[11] 4,094,914
[45] June 13, 1978

[54] PROCESS FOR THE PRODUCTION OF DIVALENT ALCOHOLS

[75] Inventors: Walter Rottig; Hans Tummes, both of Oberhausen-Sterkrade-Nord; Boy Cornils, Dinslaken; Jurgen Weber, Oberhausen-Holten, all of Germany

[73] Assignee: Ruhrchemie Aktiengesellschaft, Oberhausen-Holten, Germany

[21] Appl. No.: 685,899

[22] Filed: May 12, 1976

Related U.S. Application Data

[63] Continuation of Ser. No. 469,658, May 14, 1974, abandoned, which is a continuation of Ser. No. 193,994, Oct. 29, 1971, abandoned.

[30] Foreign Application Priority Data

Nov. 6, 1970 Germany .............................. 2054601

[51] Int. Cl.$^2$ .......................................... C07C 29/14
[52] U.S. Cl. .................................................. 568/862
[58] Field of Search ..................... 260/638 B, 635 A

[56] References Cited

U.S. PATENT DOCUMENTS

| | | | |
|---|---|---|---|
| 2,549,416 | 4/1951 | Brooks | 260/635 A |
| 2,921,940 | 1/1960 | Ramsden | 260/633 |
| 2,921,957 | 1/1960 | O'Rear et al. | 260/633 |
| 2,942,031 | 6/1960 | Kundiger | 260/633 |
| 2,951,854 | 9/1960 | Chiddix et al. | 260/633 |
| 2,978,467 | 4/1961 | Klager | 260/633 |
| 2,989,568 | 6/1961 | Russell et al. | 260/633 |
| 3,173,959 | 3/1965 | Rittmeister | 260/638 A |

FOREIGN PATENT DOCUMENTS

| | | | |
|---|---|---|---|
| 309,200 | 3/1929 | United Kingdom | 260/635 A |

*Primary Examiner*—Joseph E. Evans
*Attorney, Agent, or Firm*—Bierman & Bierman

[57] ABSTRACT

Divalent alcohols are produced by catalytic hydrogenation of a mixture comprising 20 to 40% of the corresponding hydroxyaldehyde and an organic compound. The organic compound is a solvent for and has a lower boiling point than the divalent alcohol.

9 Claims, No Drawings

PROCESS FOR THE PRODUCTION OF DIVALENT ALCOHOLS

This is a continuation of application Ser. No. 469,658, filed May 14, 1974, now abandoned which is a continuation of application Ser. No. 193,994, filed Oct. 29, 1971 now abandoned which claims the priority of German Patent Application No. P 20 54 601.4-42, filed Nov. 6, 1970.

Divalent alcohols, as for instance 1,3-propanediol, 1,3-butanediol or neopentylglycol are generally prepared by hydrogenation of the corresponding hydroxyaldehydes. The latter can be obtained by several processes. 1,3-Propanediol for instance is prepared by addition of water to acroleine; while 1,3-butanediol is prepared by aldol condensation of acetaldehyde; and neopentyglycol by aldol condensation of isobutylraldehyde and formaldehyde. The hydrogenation of the hydroxyaldehydes is generally carried out in liquid phase under elevated pressure of up to 150 atm and at temperatures of up to 200° C, preferably it is carried out with the use of nickel catalysts. (See for instance U.S. Pat. No. 2,400,724 and German Auslegeschrift No. 1,014,089).

The hydrogenation of hydroxyaldehydes in liquid phase involves some drawbacks. Owing to the relatively long contact time of the aldehyde at the catalyst, undesired byproducts may be formed which impairs the yield and purity of the resulting diols. If hydroxyaldehydes, prepared by aldol condensation, are used as starting materials, residual amounts of alkali which is present in the condensation product can damage the catalyst thereby diminishing its activity and operational life.

It is therefore an object of the invention to provide a process for the hydrogenation of hydroxyaldehydes, which overcomes the hereinbefore mentioned drawbacks and which results in obtaining the desired divalent alcohols in higher yields and higher purity and with an increased operational life of the catalyst.

It has now been found that the preparation of divalent alcohols by catalytic hydrogenation of the corresponding hydroxyaldehydes can be successfully performed if mixtures, comprising up to 50% of the hydroxyaldehyde and at least one different organic compound having a lower boiling point than that of the resulting divalent alcohols and of which at least the main component represents a solvent for the alcohol are hydrogenated in the gaseous phase in presence of hydrogenation catalysts known in the art.

Pure hydroxyaldehydes as well as technical mixtures for example mixtures obtained with industrial production of hydroxyaldehydes, may be used as starting materials with similar results. Thus, the reaction product of the aldol condensation of isobutyraldehyde and formaldehyde, said product containing, besides hydroxypivalaldehyde, isobutyraldehyde, formaldehyde and frequently methanol and water, can be, if necessary after adjustment of the concentration according to the invention of the hydroxyaldehyde, directly hydrogenated in the gaseous phase.

The presence of small amounts of water, which generally does not exceed 10% by weight, but preferably amounts to less than 5% by weight, does not injure the process according to the invention.

It is important that the concentration of the hydroxyaldehydes in the mixture to be hydrogenated does not exceed 50%. Only under this condition is a satisfactory conversion of the hydroxyaldehyde with hydrogen assured. Mixtures containing 10 to 40% by weight of hydroxyaldehyde with respect to the entire mixture are preferably used as starting materials for the hydrogenation. Since the concentration of the hydroxyaldehydes in technically available products generally ranges above the limits which must be maintained according to the invention, it is necessary under these circumstances to adjust the aldol concentration to the desired value by addition of one or more suitable organic compounds to the starting materials.

These compounds must have a boiling point lower than the respective resulting divalent alcohol and must be a good solvent for the latter. Advantageously they should also possess good solvency for the corresponding hydroxyaldehyde.

Preferred examples of these compounds include primary alcohols having 1 to 10, preferably 1 to 6 carbon atoms. These alcohols are solvents for the components present in the starting material as well as for the components present in the reaction. They are cheaply available and can be separated by ordinary distillation from the resulting divalent alcohol as well as from the by products formed during the reaction. In addition to primary alcohols, secondary alcohols can be used in the process according to the invention. Tertiary alcohols, owing to the fact that their melting points normally range above ambient temperature, are generally less suitable. In certain instances, organic compounds which react under the hydrogenation reaction conditions, may be used, in addition to alcohols which are not converted during the hydrogenation, aldehydes having 1 to 10, preferably 1 to 6 carbon atoms as well as ketones having 3 to 10, preferably 3 to 6 carbon atoms can be used.

Conventional hydrogenation catalysts based on cobalt and copper and especially on nickel are well suited for the process of the invention. The catalyst components may be deposited on carriers.

The hydrogenation is performed at temperatures between 100 and 200° C, preferably between 110° and 150° C. It is performed generally at atmospheric or at slightly increased pressure, for instance 2 to 4 atmospheres. Preferably it is carried out at a pressure of 1.5 to 2 atmospheres. The catalyst load ranges are preferably between about 0.05 and 0.3 V/Vh, more preferably between 0.08 and 0.2 V/Vh, based on the amount of hydroxyaldehyde. The amount of recycle gas per kg hydroxyaldehyde per hour should be about 5 to 15 $Nm^3$. Preferably about 9 to 12 $Nm^3$ recycle gas per kg hydroxyaldehyde per hour is used.

An especially advantageous embodiment of the process according to the invention consists in introducing the starting mixture comprising the oxyaldehyde and one or several solvents by means of a pump to an evaporator heated to temperatures ranging between 100° and 150° C while simultaneously passing the necessary amount of recycle gas as well as the additional amount of fresh hydrogen necessitated for the hydrogenation through the evaporator. By working in this manner, an especially careful treatment of the starting hydroxyaldehydes is assured, the formation of undesired by-products is substantially avoided and it is furthermore observed, that small amounts of alkali compounds, which for instance may be present in the aldolization product and are very difficult to separate without losses in yield, remain in the evaporator from which they can intermittently be removed, as for instance by rinsing with water.

According to a modified procedure, the more or less pure hydroxyaldehydes and the organic compounds serving as solvents may be separately introduced into the evaporator, thus saving the otherwise requested mixing of hydroxyaldehyde and additive components.

The following examples illustrate the process according to the invention.

EXAMPLE 1

By aldol condensation of formaldehyde (as aqueous solution) and isobutyraldehyde with addition of alkali followed by separation of the aqueous phase, a mixture consisting generally of hydroxypivalaldehyde was obtained by a known manner. A certain amount of excess isobutyraldehyde was separated from said mixture by distillation.

The remaining product had the following composition:

| | |
|---|---|
| Formaldhyde | 6.2 % by weight |
| isobutyraldehyde | 14.3 % by weight |
| methanol | 1.4 % by weight |
| intermediate runnings | 2.5 % by weight |
| hydroxypivalaldehyde | 59.2 % by weight |
| neopentylglykol | 4.0 % by weight |
| hydroxypivalic acid-neopentylglycol ester | 0.7 % by weight |
| $H_2O$ | 11.7 % by weight |

The hereinbefore mentioned product was admixed with a greater than equal weight of isobutanol and subsequently led to an evaporator provided before a hydrogenation reactor. The reactor (internal tube diameter 32 mm, tube length 3 m) was charged with 2.4 liters of a catalyst containing about 55% nickel. Two water-cooled receivers for taking up the hydrogenated raw product were connected to the hydrogenation reactor. The quantity of recycle gas amounted to 10 $Nm^3$/Kg hydroxypivalaldehyde. Fresh hydrogen was added so that a hydrogen concentration of 70 to 80% by volume in the recycle gas resulted.

At a temperature of 128° C and a catalyst load of 0.1 V/Vh, with respect to the charged hydroxypivalaldehyde, a hydroxypivalaldehyde conversion of more than 99% was obtained. The selectivity ranged between 98 and 99%. Within an operation period of 7 months, the hydrogenation temperature had to be raised only 2° C.

The water-column pressure before the hydrogenation reactor amounted to about 2 m. By increasing the pressure about 1 atmosphere the selectivity could be increased to more than 99%.

The alkali compounds contained in the raw product remained practically quantitative in the evaporator and were easily removed therefrom by rinsing with hot water in intervals of a few weeks.

EXAMPLE 2

The process set forth in example 1 was repeated with the exception, that, instead of the added isobutanol, an equal amount of isobutyraldehyde was used. The further conditions remained unchanged. A conversion of the hydroxypivalaldehyde of 97% was obtained.

EXAMPLE 3

200 $cm^3$/h of a mixture of about 85% isobutanol, about 10% hydroxypropionaldehyde as well as 5% of different compounds were led at 130° C and ordinary pressure over 200 $cm^3$ of a commercially available nickel catalyst, containing about 50% nickel arranged in a reaction tube with an internal diameter of 2.1 cm. More than 95% of the charge hydroxypropionaldehyde were converted to 1,3-propandiol.

The charged hydroxypropionaldehyde had been prepared in a known manner by addition of water to acroleine, by means of slightly acid salts.

The term V/Vh, "space velocity" as used in this specification is defined as volume of the charge per hour per catalyst volume.

The term $Nm^3$, "standard cubic meter" as used in this specification is defined as volume of a gas under standard conditions of 0° C and 760 Torr.

What we claim is:

1. In a process for preparing a divalent alcohol by the catalytic hydrogenation of the hydroxyaldehyde corresponding to said divalent alcohol, the improvement which comprises hydrogenating at a temperature of 100° to 200° C., in a gaseous phase and in the presence of a hydrogenation catalyst, a mixture comprising up to 50% of a hydroxyaldehyde obtained through the aldol condensation of unsubstituted aldehydes, and a primary or secondary alcohol having 1 to 10 carbon atoms or an aldehyde or ketone which forms said alcohol, said alcohol being a solvent for and having a lower boiling point than the divalent alcohol and further being a solvent for the hydroxyaldehyde.

2. The process as recited in claim 1 wherein the said primary or secondary alcohol has 1 to 6 carbon atoms.

3. The process as recited in claim 1 wherein the mixture comprises 20 to 40% by weight of the hydroxyaldehyde.

4. The process as recited in claim 1 wherein the hydrogenation catalyst is a nickel catalyst.

5. The process as recited in claim 1 wherein the hydrogenation is carried out at 110° to 150° C.

6. The process as recited in claim 1 wherein the hydrogenation is carried out at about 1 to 4 atmospheres.

7. The process as recited in claim 1 wherein the hydrogenation is carried out at about 1.5 to 2 atmospheres.

8. The process as recited in claim 1 wherein the hydrogenation is performed with about 5 to 15 $Nm^3$ recycle gas per hour per Kg of the hydroxyaldehyde.

9. The process as recited in claim 1 wherein the hydrogenation is performed with about 9 to 12 $Nm^3$ recycle gas per hour per Kg of the hydroxyaldehyde.

* * * * *